United States Patent [19]

Stach

[11] 4,125,542
[45] Nov. 14, 1978

[54] N-TETRAHYDROPYRANYL SUBSTITUTED PHOSPHORAMIDATES AND PHOSPHONAMIDATES

[75] Inventor: Leonard J. Stach, Riverside, Ill.

[73] Assignee: Velsicol Chemical Corporation, Chicago, Ill.

[21] Appl. No.: 798,281

[22] Filed: May 19, 1977

[51] Int. Cl.$^2$ .................. C07D 309/02; C07D 309/06; A61K 31/35
[52] U.S. Cl. .......................... 260/345.1; 260/345.9 R; 424/283
[58] Field of Search ...................... 260/345.1, 345.9 R

[56] References Cited

U.S. PATENT DOCUMENTS

| | | | |
|---|---|---|---|
| 2,972,621 | 2/1961 | McConnell et al. | 260/345.9 R |
| 3,594,405 | 7/1971 | Loux | 260/345.1 |
| 4,058,606 | 11/1977 | Kiehs et al. | 260/345.9 R |

Primary Examiner—Nicky Chan
Attorney, Agent, or Firm—Robert J. Schwarz; Dietmar H. Olesch

[57] ABSTRACT

This invention discloses new chemical compounds of the formula

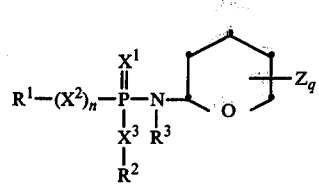

wherein $X^1$, $X^2$ and $X^3$ are each selected from the group consisting of oxygen or sulfur; $n$ is the integer 0 or 1; $R^1$ is selected from the group consisting of alkyl and

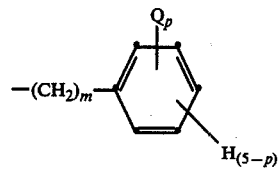

wherein $m$ is an integer from 0 to 3; Q is selected from the group consisting of alkyl, alkoxy, alkylthio, alkenyl, halogen and nitro; and $p$ is an integer from 0 to 5; $R^2$ is alkyl; $R^3$ is selected from the group consisting of hydrogen and alkyl; Z is selected from the group consisting of alkyl and alkoxy; and $q$ is the integer 0 or 1. The compounds of the above description are useful as insecticides.

9 Claims, No Drawings

N-TETRAHYDROPYRANYL SUBSTITUTED PHOSPHORAMIDATES AND PHOSPHONAMIDATES

This invention relates to new compositions of matter and more specifically relates to new chemical compounds of the formula

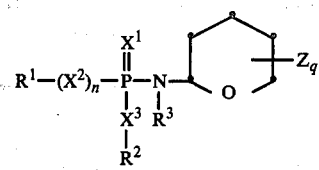

(I)

wherein $X^1$, $X^2$ and $X^3$ are each selected from the group consisting of oxygen or sulfur; $n$ is the integer 0 or 1; $R^1$ is selected from the group consisting of alkyl and

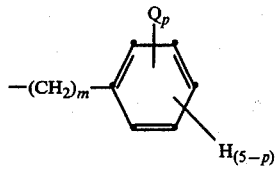

wherein $m$ is an integer from 0 to 3; Q is selected from the group consisting of alkyl, alkoxy, alkylthio, alkenyl, halogen and nitro; and $p$ is an integer from 0 to 5; $R^2$ is alkyl; $R^3$ is selected from the group consisting of hydrogen and alkyl; Z is selected from the group consisting of alkyl and alkoxy; and $q$ is the integer 0 or 1.

The compounds of the present invention are useful as insecticides.

In a preferred embodiment of the present invention $R^1$ is selected from the group consisting of lower alkyl and

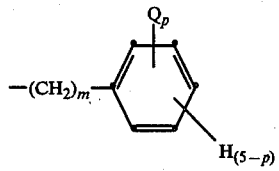

wherein $m$ is an integer from 0 to 3; Q is selected from the group consisting of lower alkyl, lower alkoxy, lower alkylthio, lower alkenyl, chlorine, bromine and nitro; and $p$ is an integer from 0 to 3; $R^2$ is selected from the group consisting of hydrogen and lower alkyl; Z is selected from the group consisting of lower alkyl and lower alkoxy; and $q$ is the integer 0 or 1.

The term lower as used herein designates a straight or branched hydrocarbon chain of up to six carbon atoms.

The compounds of the present invention can be prepared by reacting a phosphorous compound of the formula

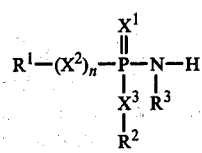

(II)

wherein $X^1$, $X^2$, $X^3$, $n$, $R^1$, $R^2$ and $R^3$ are as heretofore described with an excess molar amount of a dihydropyran of the formula

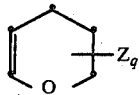

(III)

wherein Z and $q$ are as heretofore described. This reaction can be effected by combining the phosphorus compound of formula II with the dihydropyran of formula III in the presence of a catalytic amount of toluenesulfonic acid. The reaction mixture can then be heated at elevated temperatures ranging up to the reflux temperature of the mixture for a period of from about 1 to about 8 hours. After this time base such as sodium carbonate can be added to neutralize the catalyst. The desired product can then be recovered by distillation from the reaction mixture.

Exemplary compounds of formula II useful in preparing the compounds of the present invention are:

O,O-dimethyl thionophosphoramidate, O,O-diethyl thionophosphoramidate, O-methyl O-ethyl phosphoramidate, O-methyl S-ethyl thiolophosphoramidate, O-phenyl S-methyl thiolophosphoramidate, O-(4-chlorophenyl) S-methyl thiolophosphoramidate, O-(2-methylphenyl) S-methyl thiolophosphoramidate, O-(3-allylphenyl) S-methyl thiolophosphoramidate, O-(4-methylthiophenyl) S-methyl thiolophosphoramidate, O-(2-methoxyphenyl) S-methyl thiolophosphoramidate, O-(3-nitrophenyl) O-methyl phosphoramidate, O-(2,4,6-trichlorophenyl) O-methyl phosphoramidate, O-(4-bromophenyl) O-methyl phosphoramidate, O-(2-methyl-4-chlorophenyl) O-methyl phosphoramidate, O-methyl methylthionophosphonamidate, S-ethyl methylthionothiolophosphonamidate, O-propyl benzylthionophosphonamidate, S-butyl benzethylthiolophosphonamidate, O-hexyl 4-chlorophenylphosphonamidate, O-ethyl 3,4-dichlorophenylthionophosphonamidate, S-ethyl 4-nitrophenylthiolophosphonamidate, S-ethyl 3-methylthiophenylthiolosphosphonamidate, S-ethyl 4-ethylthiophenylthiolosphosphonamidate, S-ethyl 4-allylphenylthiolosphosphonamidate, S-ethyl 3-hex-4-enyphenylthiolosphosphonamidate, S-ethyl 2-ethoxyphenylthiolosphosphonamidate, S-ethyl 4-hexyloxyphenylthiolosphosphonamidate.

Exemplary compounds of formula III useful for preparing the compounds of the present invention are dihydropyran, 3,4-dihydro-2-methoxy-2H-pyran, 3,4-dihydro-2-ethoxy-2H-pyran, 5,6-dihydro-4-methoxy-2H-pyran, 3,4-dihydro-2-methyl-2H-pyran, 3,4-dihydro-2-ethyl-2H-pyran and the like.

The manner in which the compounds of the present invention can be prepared is more specifically illustrated in the following examples.

EXAMPLE 1

Preparation of O,S-Dimethyl N-Tetrahydropyran-2-ylthiolophosphoramidate

O,S-Dimethyl thiolophosphoramidate (4.0 grams; 0.028 mole), dihydropyan (10 ml) and catalyst consisting of 8 drops of a solution of toluenesulfonic acid (1 gram) in ether (100 ml) were charged into a glass reaction vessel equipped with a mechanical stirrer, thermometer and reflux condenser. The reaction mixture was heated at reflux with continuous stirring for a period of about 2 hours. After this time the reaction mixture was allowed to stand at room temperature for 2 days. Sodium carbonate was then added to the reaction mixture to neutralize the catalyst. The reaction mixture was then filtered and the filtrate was stripped of unreacted starting material under reduced pressure leaving a solid residue. The residue was stirred in hexane and was filtered to yield the desired product O,S-dimethyl N-tetrahydropyran-2-ylthiolophosphoramidate having a melting point of 42° to 45° C.

EXAMPLE 2

Preparation of O,O-Dimethyl N-Tetrahydropyran-2-ylthionophosphoramidate

O,O-Dimethyl thionophosphoramidate (5 grams), dihydropyran (10 grams) and catalyst (7 drops) consisting of toluenesulfonic acid (1 gram) dissolved in ether (100 ml) were charged into a glass reaction vessel equipped with a magnetic stirrer, thermometer and reflux condenser. The reaction mixture was first stirred at room temperature for 30 minutes and then at its reflux temperature for an additional 30 minutes. After this time the mixture was cooled to room temperature and sodium carbonate (1 gram) was added with stirring. The reaction mixture was then distilled to yield the desired product O,O-dimethyl N-tetrahydropyran-2-ylthionophosphoramidate as a colorless oil having a boiling point of 99° to 101° C. at 0.10 mm of Hg pressure.

EXAMPLE 3

Preparation of O,S-Diethyl N-Tetrahydropyran-2-ylthiolophosphoramidate

O,S-Diethyl thiolophosphoramidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product O,S-diethyl N-tetrahydropyran-2-ylthiolophosphoramidate.

EXAMPLE 4

Preparation of O-Methyl S-Ethyl N-Tetrahydropyran-2-ylthiolophosphoramidate

O-Methyl S-ethyl thiolophosphoramidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product O-methyl S-ethyl N-tetrahydropyran-2-ylthiolophosphoramidate.

EXAMPLE 5

Preparation of O-Phenyl S-Ethyl N-6-Methoxytetrahydropyran-2-yl-thiolophosphoramidate O-Phenyl S-ethyl thiolophosphoramidate (0.03 mole), 3,4-dihydro-2-methoxy-2H-pyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product O-phenyl S-ethyl N-6-methoxytetrahydropyran-2-ylthiolophosphoramidate.

EXAMPLE 6

Preparation of O-(2-Methylphenyl) S-Ethyl N-6-Methyltetrahydropyran-2-ylthiolophosphoramidate O-(2-Methylphenyl) S-ethyl thiolophosphoramidate (0.03 mole), 3,4-dihydro-2-methyl-2H-pyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product O-(2-methylphenyl) S-ethyl N-6-methyl-tetrahydropyran-2-ylthiolophosphoramidate.

EXAMPLE 7

Preparation of S-(4-Nitrophenyl) O-Methyl N-Tetrahydropyran-2-ylthiolophosphoramidate S-(4-Nitrophenyl) O-methyl thiolophosphoramidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product S-(4-nitrophenyl) O-methyl N-tetrahydropyran-2-ylthiolophosphoramidate.

EXAMPLE 8

Preparation of O-Ethyl N-(Tetrahydropyran-2-yl)methylthionophosphonamidate

O-Ethyl methylthionophosphonamidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product O-ethyl N-(tetrahydropyran-2-yl)methylthionophosphonamidate.

EXAMPLE 9

Preparation of O-Ethyl N-(Tetrahydropyran-2-yl)-3,4-dichlorophenylthionophosphonamidate O-Ethyl 3,4-dichlorophenylthionophosphonamidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product O-ethyl N-(tetrahydropyran-2-yl)-3,4-dichlorophenylthionophosphonamidate.

EXAMPLE 10

Preparation of O-Isopropyl N-(Tetrahydropyran-2-yl)-4-nitrophenylthionophosphonamidate O-Isopropyl 4-nitrophenylthionophosphonamidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product O-isopropyl N-(tetrahydropyran-2-yl)-4-nitrophenylthionophosphonamidate.

EXAMPLE 11

Preparation of S-Methyl N-(Tetrahydropyran-2-yl)-3-methylthiophenylthiolophosphonamidate S-Methyl 3-methylthiophenylthiolophosphonamidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product S-methyl N-(tetrahydropyran-2-yl)-3-methylthiophenylthiolophosphonamidate.

EXAMPLE 12

Preparation of S-Ethyl N-(Tetrahydropyran-2-yl)-2-methoxyphenylthiolophosphonamidate S-Ethyl 2-methoxyphenylthiolophosphonamidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product S-ethyl N-(tetrahydropyran-2-yl)-2-methoxyphenylthiolophosphonamidate.

EXAMPLE 13

Preparation of S-Isopropyl N-(Tetrahydropyran-2-yl)-3-allylphenylthiolophosphonamidate S-Isopropyl 3-allylphenylthiolophosphonamidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product S-isopropyl N-(tetrahydropyran-2-yl)-3-allylphenylthiolophosphonamidate.

EXAMPLE 14

Preparation of O-Methyl O-[3-(4-Bromophenyl)propyl] N-Tetrahydropyran-2-ylthionophosphoramidate O-Methyl O-[3-(4-bromophenyl)propyl] thionophosphoramidate (0.03 mole), dihydropyran (10 ml) and catalyst (8 drops) consisting of a solution of toluenesulfonic acid (1 gram) dissolved in ether (100 ml) are charged into a glass reaction vessel equipped with a mechanical stirrer, thermometer and reflux condenser. The reaction mixture is heated at reflux with stirring for a period of about 3 hours. After this time the mixture is cooled to room temperature and sodium carbonate (1 gram) is added with stirring. The reaction mixture is then filtered and the filtrate is distilled to yield the desired product O-methyl O-[3-(4-bromophenyl)propyl] N-tetrahydropyran-2-ylthionophosphoramidate.

Additional exemplary compounds within the scope of the present invention which can be prepared by the procedures of the foregoing examples are:

O-methyl O-(2,4-diethylphenyl) N-tetrahydropyran-2-ylthionophosphoramidate, O-ethyl O-(3-propylphenyl) N-6-ethyltetrahydropyran-2-ylthionophosphoramidate, O-propyl-O-(4-butylphenyl) N-6-propyltetrahydropyran-2-ylthionophosphoramidate, O-n-butyl O-(4-pentylphenyl) N-6-hexyltetrahydropyran-2-ylthionophosphoramidate, O-t-butyl O-(4-hexylphenyl) N-6-propoxytetrahydropyran-2-ylthionophosphoramidate, O-pentyl O-(2-ethoxyphenyl) N-6-pentyloxytetrahydropyran-2-ylthionophosphoramidate, O-hexyl O-(3-butoxyphenyl) N-6-hexyloxytetrahydropyran-2-ylthionophosphoramidate, O-methyl O-(4-hexyloxyphenyl) N-tetrahydropyran-2-ylthionophosphoramidate, O-ethyl O-(3-ethylthiophenyl) N-tetrahydropyran-2-ylthionophosphoramidate, O-ethyl O-(4-butylthiophenyl) N-tetrahydropyran-2-ylthionophosphoramidate, O-ethyl S-(4-hexylthiophenyl) N-tetrahydropyran-2-ylthiolophosphoramidate, O-ethyl S-(3-but-3-enylphenyl) N-tetrahydropyran-2-ylthiolophosphoramidate, O-ethyl S-(4-pent-3-enylphenyl) N-tetrahydropyran-2-ylthiolophosphoramidate, O-ethyl S-(4-hex-4-enylphenyl) N-tetrahydropyran-2-ylthiolophosphoramidate, O,S-dimethyl-N-tetrahydropyran-2-ylthiolothionophosphoramidate, O-ethyl S-n-propyl N-tetrahydropyran-2-ylthiolophosphoramidate and the like.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect infestation. The emulsifiers most commonly used in these concentrates are nonionic or mixtures of nonionic with anionic surface-active agents.

A typical insecticidal composition according to this invention is illustrated by the following example, in which the quantities are in parts by weight.

EXAMPLE 15

| Preparation of a Dust | |
| --- | --- |
| Product of Example 1 | 10 |
| Powdered talc | 90 |

The above ingredients are mixed in a mechanical grinder-blender and are ground until a homogeneous, free-flowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to about 95 percent of the active ingredients in the insecticidal compositions. Use of the combinations of these other insecticides with the compounds of the present invention provides insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol and the like; organic phosphorus compounds such as TEPP, schradan, ethion, parathion, methyl parathion, EPN, demeton, carbophenothion, phorate, zinophos, diazinon, malathion, mevinphos, dimethoate, DBD, ronnel, oxydemeton-methyl, dicapthon, chlorothion, phosphamidon, naled, fention, trichlorofon, DDVP and the like; organic nitrogen compounds such as dinitro-o-cresol, dinitrocyclohexylphenol, DNB, DNP, binapacril, azobenzene and the like; organic carbamate compounds such as carbaryl, ortho 5353 and the like; organic sulfur compounds such as phenothiazine, phenoxathin, lauryl thiocyanate, bis(2-thiocyanoethyl)ether, isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like; while examples of nematocidal compounds are chloropicrin, O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plant surfaces are taken up by the plant, and the insects are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beef leaf miner, and gall insects such as the wheat joint worm and the grape phylloxera. Insects which attach below the surface of the ground are classified as subterranean insects and include such destructive pests as the wooly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

The insecticidal activity of the compounds of the present invention was demonstrated by experiments carried out for the control of a variety of insects.

Housefly

Approximately 25 to 30 4-day-old Housefly adults are placed in spherical wire mesh cages. The cages are mounted at the center of a rotating turntable so that each cage rotates on its own axis. At least three cages are provided for each test unit. Individual rotating cages are sprayed with aerosol formulations of the test compound at the indicated concentrations. Houseflies are then immediately removed to observation cages, observed for 60-minute knockdown, supplied sugar-water food source, transferred to a holding room and observed for mortality 24 hours after treatment. The results of this test are shown in Table I.

TABLE I

| Test Compound | Rate (ppm): | Percent Control | | | | |
|---|---|---|---|---|---|---|
| | | 1024 | 512 | 256 | 128 | 64 |
| Product of Example 1 | k | 80* | 10* | 10* | 0* | 0 |
| | m | 100* | 100* | 100* | 80* | 80 | k = 60-minute knockdown
m = 24-hour mortality
*Values are averages of two replicates.

Southern Armyworm

Foliar portions of potted Dwarf Horticultural bean plants in first true leaf growth stage are sprayed with test solution containing a compound of this invention. The pots are then placed in holding racks provided with a subterranean water source. Three test plants are used for each test unit. Five third-instar larvae of Southern Armyworm are caged on treated plants for 48 hours. After this time observations are made for insect mortality. The results of this procedure are set forth in Table II.

TABLE II

| Test Compound | Rate (ppm): | Percent Control | | | | |
|---|---|---|---|---|---|---|
| | | 1024 | 512 | 256 | 128 | 64 |
| Product of Example 1 | | 100* | 95* | 90* | 55* | 0 |

*Values are averages of two replicates.

Mexican Bean Beetle

Foliar portions of potted Dwarf Horticultural bean plants in first true leaf growth stage are sprayed with test solution containing a compound of this invention, and in some cases the soil of the potted plants is also drenched with an aqueous emulsion of the test compound. The pots are then placed in holding racks provided with a subterranean water source. Three test plants are used for each test unit. Five third-instar larvae of Mexican Bean Beetle are caged on treated plants for 48 hours. After this time observations are made of insect mortality. The results of these experiments are summarized in Table III.

TABLE III

| Test Compound | Percent Control | | | | | | | |
|---|---|---|---|---|---|---|---|---|
| | Rate (ppm) | | | | | | | |
| | 1024 | 512 | 256 | 128 | 64 | 32 | 16 | 8 |
| Product of Example 1 | 100* | 100* | 85* | 85* | 45* | 20 | 10 | 0 |

*Values are averages of two replicates.

Boll Weevil

Two leaves of a cotton plant are sprayed with test solution containing a compound of this invention at the indicated rates and are allowed to air dry. Boll weevils are then placed on the surface of the leaves, and the infested leaves are kept in a petri dish and are held for a period of 48 hours. After this time mortality is observed and compared to untreated controls. The results of these tests are shown in Table IV.

TABLE IV

| Test Compound | Rate (ppm): | Percent Control | | | | |
|---|---|---|---|---|---|---|
| | | 1024 | 512 | 256 | 128 | 64 |
| Product of Example 1 | | 80* | 60* | 20* | 10* | 0 |

*Values are averages of two replicates.

Two-Spotted Spider Mite

Potted horticultural beans at growth stage when primary leaves are approximately 1 inch long are infested with two-spotted spider mites 24 hours prior to treatment, ensuring establishment of adults and egg deposition at time of treatment.

The candidate compound is dissolved in a suitable solvent (acetone, methanol or other) or prepared as a wettable powder and diluted to appropriate concentrations with deionized water containing wetting and/or dispersing agents as appropriate.

Infested host plants, as above, are sprayed with test solution containing a compound of this invention. The pots are then placed in holding racks provided with a subterranean water source. Mortality is determined 48 hours after treatment by removing and observing one leaf from each plant. The results of these tests are set forth in Table V.

TABLE V

| Test Compound | Rate (ppm): | \multicolumn{5}{c|}{Percent Control} |
|---|---|---|---|---|---|---|
| | | 1024 | 512 | 256 | 128 | 64 |
| Product of Example 1 | | 80* | 75* | 65* | 45* | 80 |

*Values are averages of two replicates.

Cabbage Looper

Ten- to 14-day-old Henderson bush lima bean plants are planted in 3½ inch plastic pots using potting soil capped with ¼ inch of sand. The bean plants are then placed on a turntable and are sprayed with 100 ml of an aqueous solution or dispersion of a compound of this invention at the indicated concentrations. The plants are allowed to dry, and a leaf is removed from each and placed in a petri dish on top of a piece of wetted filter paper. Ten third-instar larvae of the Cabbage Looper are then placed on the leaf, and the petri dish is covered. Observations of mortality are made after 48 hours and are compared to untreated controls. Results of these tests are shown in Table VI.

TABLE VI

| Test Compound | Rate (ppm): | \multicolumn{4}{c|}{Percent Control} |
|---|---|---|---|---|---|
| | | 1024 | 512 | 256 | 128 |
| Product of Example 1 | | 90 | 80 | 50 | 20 |

Yellow Fever Mosquito Larvae

Aliquots of 100 ml of tap water containing various concentrations of compounds of this invention are each supplied with 20 1-day-old Yellow Fever Mosquito larvae (*aedes aegypti L.*). The larvae are maintained at 25° C. and are fed with malt yeast powder. After 13 days, when the pupae of untreated insects have hatched, the mortality percentages are calculated in comparison with the untreated controls. The results are indicated in Table VII.

TABLE VII

| Test Compound | Rate (ppm): | \multicolumn{4}{c|}{Percent Control} |
|---|---|---|---|---|---|
| | | 10 | 1 | .1 | .01 |
| Product of Example 1 | | 50* | 35* | 25* | 15* |

*Values are averages of two replicates.

Pea Aphid

Windsor Broad Bean plants grown under greenhouse conditions, in the first true leaf growth stage and in soil of low moisture content are sprayed with test solution containing a compound of this invention. The pots are then placed in holding racks provided with a subterranean water source. Adult pea aphids are transferred to the foliar portion of the treated plants and held there for a period of 48 hours. After this time insect mortality is determined by observation in comparison to controls. The results of these procedures are shown in Table VIII.

TABLE VIII

| Test Compound | Rate (ppm): | \multicolumn{8}{c|}{Percent Control} |
|---|---|---|---|---|---|---|---|---|---|
| | | 1024 | 512 | 256 | 128 | 64 | 32 | 16 | 8 |
| Product of Example 1 | | 100* | 100* | 100* | 95* | 90* | 85* | 72* | 69* |

*Values are averages of two replicates.

Green Peach Aphid

Dwarf Nasturtiums are planted in 3½ inch plastic pots containing potting soil capped with ¼ inch of sand. Ten- to 14-day-old plants are placed on a revolving table in a mist chamber and sprayed with 100 ml of a solution containing a compound of this invention at the indicated concentrations. After the leaves have dried, an untreated leaf infested with 10 to 20 Green Peach Aphids is placed on a treated leaf. As the untreated leaf wilts, the aphids crawl onto the treated leaf. Mortality is recorded in comparison to untreated controls 48 hours after infestation of the treated plant. The results of these tests are set forth in Table IX.

TABLE IX

| Test Compound | Rate (ppm): | \multicolumn{8}{c|}{Percent Control} |
|---|---|---|---|---|---|---|---|---|---|
| | | 1024 | 512 | 256 | 128 | 64 | 32 | 16 | 8 |
| Product of Example 1 | | 100* | 100* | 100* | 97.5* | 90* | 90* | 90* | 85* |

*Values are averages of two replicates.

German Cockroach

Ten adult German cockroaches are first anesthetized with carbon dioxide and thereafter dipped into a 100 ml solution of the test compound at the indicated concentrations. Thereafter the cockroaches are placed in holding cups and supplied with water as required. Mortality of the roaches is observed 60 minutes, 24, 48 and 72 hours after treatment in comparison to untreated controls. The results of these tests are shown in Table X.

TABLE X

| Test Compound | Rate (ppm) | \multicolumn{5}{c|}{Percent Control} |
|---|---|---|---|---|---|---|
| | | 256 | 128 | 64 | 32 | 16 |
| Product of Example 1 | 60 | 0 | 0 | 0 | 0 | 0 |
| | 24 | 70 | 30 | 10 | 0 | 10 |
| | 48 | 90 | 90 | 60 | 20 | 30 |
| | 72 | 90 | 90 | 70 | 20 | 30 |

TABLE XI

| | \multicolumn{9}{c|}{SOIL DRENCH} |
|---|---|---|---|---|---|---|---|---|---|
| | \multicolumn{9}{c|}{Rate #/A} |
| Product of Example 1 | | | | | | | | | |
| Insect Species | \multicolumn{9}{c|}{Percent Control} |
| | 64 | 32 | 16 | 8 | 4 | 2 | 1 | .5 | .25 | .125 |
| CAL | 20 | — | — | — | — | — | — | — | — | — |
| SAW | 95* | 100 | 80 | 40 | 40 | — | — | — | — | — |

TABLE XI-continued

SOIL DRENCH
Rate #/A

Product of Example 1

| Insect Species | | Percent Control | | | | | | | | |
|---|---|---|---|---|---|---|---|---|---|---|
| | | 64 | 32 | 16 | 8 | 4 | 2 | 1 | .5 | .25 | .125 |
| MBB | | 100* | 100 | 80 | 80 | 70 | — | — | — | — | — |
| GPA | | 100* | 100 | 100 | 100 | 100 | — | 100 | 100 | 95 | 95 |
| PA | | 100* | 100 | 100 | 100 | 100 | — | — | — | — | — |
| TSM | | 100* | 95 | 90 | 80 | 35 | — | — | — | — | — |
| SCR | 24h | — | — | — | 70* | 60* | 70* | 60* | 50* | 20 | — |
| | 72h | — | — | — | 90* | 70* | 70* | 70* | 50* | 60 | — |

*Values are averages of two replicates.
CAL = Cabbage Looper
SAW = Southern Armyworm
MBB = Mexican Bean Beetle
GPA = Green Peach Aphid
PA = Pea Aphid
TSM = Two-Spotted Spider Mite
SCR = Southern Corn Rootworm

I claim:

1. A compound of the formula $$R^1-(X^2)_n-\underset{\underset{R^2}{|}}{\overset{\overset{X^1}{\|}}{P}}-\underset{R^3}{N}\underset{O}{\diagdown}Z_q$$

wherein $X^1$, $X^2$ and $X^3$ are each selected from the group consisting of oxygen or sulfur; $n$ is 1; $R^1$ is selected from the group consisting of alkyl and $$-(CH_2)_m-\bigcirc\!\!\!\!\!\!\!\!\!\!\!\!\!\!\!\!\!\!\!\!\underset{H_{(5-p)}}{Q_p}$$

wherein $m$ is an integer from 0 to 3; Q is selected from the group consisting of alkyl, alkoxy, alkylthio, alkenyl, halogen and nitro; and $p$ is an integer from 0 to 5; $R^2$ is alkyl; $R^3$ is selected from the group consisting of hydrogen and alkyl; Z is selected from the group consisting of alkyl and alkoxy; and *q is the integer* 0 or 1.

2. The compound of claim 1, O,S-dimethyl N-tetrahydropyran-2-ylthiolophosphoramidate.

3. The compound of claim 1, O,O-dimethyl N-tetrahydropyran-2-ylthionophosphoramidate.

4. The compound of claim 1, O,S-diethyl N-tetrahydropyran-2-ylthiolophosphoramidate.

5. The compound of claim 1, O-methyl S-ethyl N-tetrahydropyran-2-ylthiolophosphoramidate.

6. The compound of claim 1, O-phenyl S-ethyl N-6-methoxytetrahydropyran-2-ylthiolophosphoramidate.

7. The compound of claim 1, O-(2-methylphenyl) S-ethyl N-6-methyltetrahydropyran-2-ylthiolophosphoramidate.

8. The compound of claim 1, S-(4-nitrophenyl) O-methyl N-tetrahydropyran-2-ylthiolophosphoramidate.

9. The compound of claim 1, O,S-dimethyl N-tetrahydropyran-2-ylthiolothionophosphoramidate.

* * * * *